US00PP13630P29

(12) United States Plant Patent
Fleming

(10) Patent No.: US PP13,630 P2
(45) Date of Patent: Mar. 11, 2003

(54) HIBISCUS PLANT NAMED 'OLD YELLA'

(76) Inventor: David Whitman Fleming, deceased, late of Lincoln, NE (US), by Gretchen A. Zwetzig, executor, Lincoln NE.

( * ) Notice: Subject to any disclaimer, the term of this patent is extended or adjusted under 35 U.S.C. 154(b) by 0 days.

(21) Appl. No.: 09/607,101

(22) Filed: Jun. 29, 2000

(51) Int. Cl.[7] ..... A01H 5/00

(52) U.S. Cl. ..... Plt./257

(58) Field of Search ..... Plt./257

(56) References Cited

PUBLICATIONS

UPOV–ROM GTITM computer database, GTI JOUVE retrieval software, 2001/02, citations for 'Old Yella'.*

* cited by examiner

*Primary Examiner*—Bruce R. Campell
*Assistant Examiner*—W C Haas

(57) ABSTRACT

A new and distinct cultivar of winter hardy hibiscus plant named 'Old Yella' is the result of a unique hybridization. This new and distinct cultivar is characterized primarily as to novelty by its extreme cold hardiness to Zone 4, its large, thick-textured, pale yellow flowers and its green-leaved plants with bright yellow buds before onset of flowering, its vigorous and uniform growth habit, and its floriferous nature from midsummer until frost.

1 Drawing Sheet

BACKGROUND OF THE NEW PLANT

The new plant of this invention is the result of a unique hybridization, with the breeding achievement being evidenced in the outstanding combination of characteristics exhibited by this new and distinct Hibiscus plant, which include:

(a) Refined ovate, green leaves which have relatively smooth margins and yellow buds all over the plant which compliments the landscape;

(b) Large flowers that are outstanding for their pale yellow, thick-textured petals with dark burgandy centers and medium to heavy ruffling;

(c) The plant being very floriferous with flowers that stay open at least one full day;

(d) The plant being medium-sized, but vigorous with compact and uniform breaking action which gives it unique landscape utility; and (e) The plant being so hardy that it can consistently withstand winter temperatures at least −30 degrees Fahrenheit.

SUMMARY OF THE INVENTION

'Old Yella' was the result of a 40-year breeding program. Its ancestry includes *Hibiscus moscheutos*. More specifically, the plant resulted from multiple crossings with 'Bright Eye', a Fleming variety (non-patented which is a *Hibiscus moscheutos*. The seedling which most nearly met all of the above named standards was selected.

This new plant first bloomed in the summer if 1986 and was selected by David Fleming and Gretchen Zwetzig on David Fleming's property in Lincoln, Nebr. Asexual propagation of the plant by cuttings and root division has shown that the unique and distinguishing features of the plant are faithfully transmitted from generation to generation and appear to be fixed.

Since its origin, the plant has bloomed from midsummer until frost, while exhibiting the aforementioned distinctive characteristics. This hardy Hibiscus plant greatly contributes to the market with its sheer beauty and utter refinement, its compact growth habit, its enhanced resistance to disease and insects, its stability through extremes in rain and drought, and its extreme hardiness.

BRIEF DESCRIPTION OF THE DRAWINGS

The flower, bud, foliage, and growth habit of the cultivar are shown in the attached photograph, More specifically, the photograph is a close-up of the flower and the leaf.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with the *Dictionary of Color* (Maerz and Paul), while general color recitations are consistent with ordinary American color terminology.

'Old Yella' has not been observed under all possible environment conditions. It is to be understood that the phenotype may vary significantly with variations in environment such as temperature, light intensity, and day length, and day length, without, however any difference in genotype of the plant. The following botanical characteristics and observations are gathered from the plant when grown in Lincoln, Nebr. (USDA Zone 4).

THE PLANT

Parentage

*Seed parent.*—*Hibiscus moscheutos* 'Bright Eye'.

*Pollen parent.*—*Hibiscus moscheutos* 'Bright Eye'.

Origin: A selected seedling from a stated cross.

Type of plant: Hardy, herbaceous perennial.

Classification: Variety of Hibiscus plant.

Propagation: Relatively easy to propagate; holds its distinguishing characteristics through successive cuttings and divison.

Size: About 3½–4 feet tall and about 2½ ft. wide.
Form: Symmetrical annual growth from perennial roots.
Habit: Upright and uniformly branched.
Growth: Vigorous; medium and compact. Full grown (4 ft.) in 2 years.
Hardiness: Hardy to at least −30 degrees Fahrenheit.
General health: Plant is very disease resistant against rot, aphids, spider mites, scale, white fly, etc.; sturdy through excessive drought, rain, or wind.
Propagation: Relatively easy and fast rooting in approximately 2 weeks.
Foliage:
1. *Arrangement.*—Alternate.
2. *Shape.*—Juvenile: Variable, ovate leaf. Rounded base shape. Mature: Refined, ovate leaf with entire to mildly serrate margins and acute apices; rounded base.
3. *Size.*—Mature leaf (petiole base to apex): Length is about 6½ inches or 16 cm, width is about 5 inches or 13 cm.
4. *Color.*—Young leaves (upper side): slightly lighter than L-11, PLATE 22, page 67, "Paradise". Mature leaves: (upper side) — slightly darker than I-11, PLATE 22, page 67, "Paradise". Veins: K-1, PLATE 46, page 115. Coloration of the lower leaf surface: Slightly lighter than F-7, PLATE 22, page 67.
5. *Surface texture.*—Low sheen.
6. *Petiole length.*—About 2½ inches or 8 cm.
7. *Petiole color.*—Green to K-1, PLATE 46, page 115.

Stems: The stems are stout at the base, becoming more slender toward the apices; coloration is consistent with the petiole.

THE FLOWER

Blooming period: Profuse from July until frost.
Flower diameter: Large; about 12 inches, (24 cm).
Borne: Singly in leaf axils, from midpoint of stems upward.
Bloom duration: Individual bloom lasts at least one full day.
Form: Campanulate; petals are also very overlapping.
Bud:
1. *Length.*—About 1¾ inches (or 4 cm) on day before opening.
2. *Color.*—J-1, PLATE 10, page 43, "Sulfur".
3. *Surface texture.*—Semi-glabrous.
4. *Duration.*—One to two weeks.

Corolla: Having 5 petals.
1. *Petal character and dimensions.*—Campanulate and very overlapping. Length is about 5 inches or 12.5 cm. Width is about 4½ inches or 11.5 cm.
2. *Coloration.*—Pale, luminescent yellow with a burgundy red center. (a) Pale yellow petals: C-1, PLATE 10, page 43. Coloration of lower petal surface: C-1, PLATE 10, page 43. (b) Veination in petals: Slightly lighter than C-1, PLATE 10, page 43. (c) Eye Zone: H-6, PLATE 7, page 37.
3. *Texture.*—Smooth.
4. *Substance.*—Thick.
5. *Shape.* —Campanulate and very overlapping.

Reproductive organs:
1. *Staminal column.*—Stamen along basal two-thirds. Stamen length: About 1½ inches (or 4 cm). Stamen color: A-1, PLATE 1, page 25. Pollen color: D-1, PLATE 9, page 41.
2. *Style.*—Terminates upper one-third of staminal coumn. Stigmatic lobe color: G-1, PLATE 9, page 41.

Calyx: Connate at the base; about 2 inches (or 9 cm) in length.
Color: Medium green.
Stipules: None.
Epicalyx: Whorl of bracts.
1. *Shape.*—10 to 12 slender, sword-shaped bractlets.
2. *Length.*—About 1¾ inches (or 4 cm).
3. *Color.*—K-8, PLATE 19, page 61.

Penduncle:
1. *Length.*—About 1½ inches (or 4 cm).
2. *Strength.*—Stiff and sturdy.
3. *Color.*—Light to medium green.

GENERAL OBSERVATIONS

This plant, as a hybridized hardy Hibiscus, is valuable to the landscape market for its improvements in thicker-textured and uniquely colored flowers and buds, refined green foliage on a more compact plant, its all-around vigor, good braking action, and adaptation to extreme environments, including the ability to consistently survive winter temperatures of at least −30 degrees Fahrenheit.

It is claimed:

1. A new and distinct cultivar of Hibiscus plant, as herein shown and described, characterized by its compact nature, refined green, ovate foliage, its large, ruffled, pale yellow flowers and yellow buds, its vigor, and its hardiness.

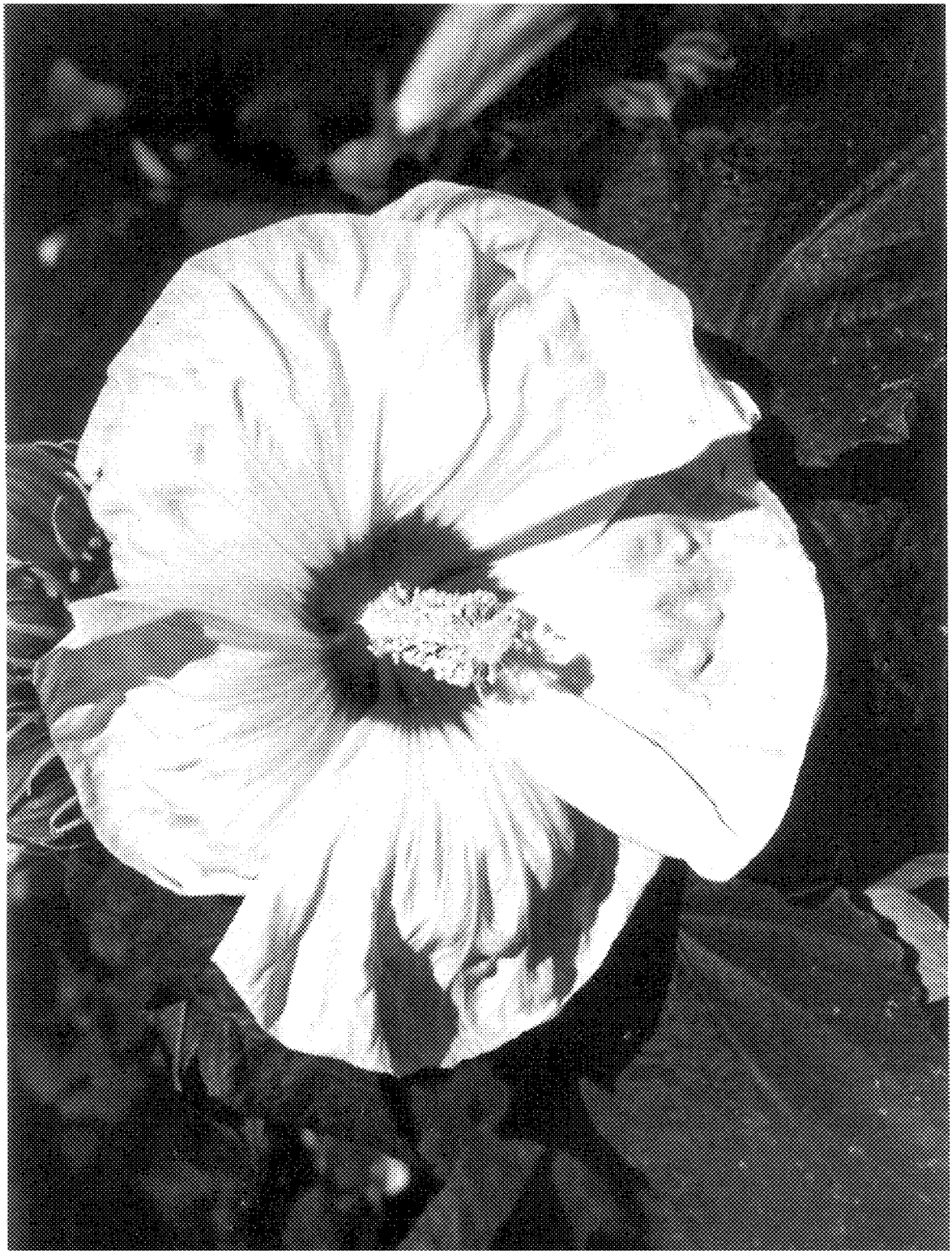

* * * * *